United States Patent [19]

Manz et al.

[11] Patent Number: 5,599,432
[45] Date of Patent: Feb. 4, 1997

[54] DEVICE AND A METHOD FOR THE ELECTROPHORETIC SEPARATION OF FLUID SUBSTANCE MIXTURES

[75] Inventors: Andreas Manz, Bettingen, Switzerland; Carlo S. Effenhauser, Weil am Rhein, Germany

[73] Assignee: Ciba-Geigy Corporation, Tarrytown, N.Y.

[21] Appl. No.: 335,610

[22] Filed: Nov. 8, 1994

[30] Foreign Application Priority Data

Nov. 11, 1993 [CH] Switzerland ............................ 3392/93

[51] Int. Cl.⁶ ......................... G01N 27/26; G01N 27/447
[52] U.S. Cl. ............................................ 204/451; 204/601
[58] Field of Search ............................ 204/180.1, 299 R, 204/182.8, 182.9, 183.2, 182.1, 451, 601

[56] References Cited

U.S. PATENT DOCUMENTS

| | | | |
|---|---|---|---|
| 4,385,974 | 5/1983 | Shevitz | 204/182.1 |
| 4,908,112 | 3/1990 | Pace | 204/601 X |
| 5,131,998 | 7/1992 | Jorgenson et al. | 204/299 R |
| 5,240,577 | 8/1993 | Jorgenson et al. | 204/180.1 |
| 5,296,114 | 3/1994 | Manz | 204/451 |
| 5,328,578 | 7/1994 | Gordon | 204/180.1 |
| 5,389,221 | 2/1995 | Jorgenson et al. | 204/299 R |

FOREIGN PATENT DOCUMENTS 9317771  9/1993  WIPO .

OTHER PUBLICATIONS

X. Huang et al, Anal. Chem. vol. 64, 1992 No Month Available pp. 967–972.
A. T. Andrews, Oxford Science Publications, Monographs on Physical Biochemistry, (1981) No Month Available pp. 222–231.
Journal of Chromatography Library vol. 52 S.F.Y. Li, (1993) No Month Available pp. 172–199 and Contents.
A. V. Lemmee et al. 266b Analy. Chem. 65 (1993) No Month Available No. 11 pp. 1577–1581.
N. Burggraf et al. HRC Jour. of High Resolution Chromatography 16, 1993 No Month Available, No. 10 pp. 594–596.
C. Effenhauser et al. Analy. Chem., 65, (1993) No Month Available No. 19 pp. 2637–2642.
James W. Jorgenson et al "Two-dimensional Separations of Peptides and Proteins by Comprehensive Liquid Chromatography–Capillary Electrophoresis" Electrophoresis, vol. 14, No. 5–6 (May/Jun. 1993) 439–447.

(List continued on next page.)

Primary Examiner—Donald R. Valentine
Assistant Examiner—John S. Starsiak, Jr.
Attorney, Agent, or Firm—George R. Dohmann

[57] ABSTRACT

A device for the electrophoretic separation of complex fluid substance mixtures comprises a channel system (21, 2, 22) for a carrier medium (C), an injection device (3) for the injection into the carrier medium (C) of a substance mixture (S) to be separated, and a separating path (2) for the separation of the substance mixture (S) in an electric field applied along the separating path (2). Downstream of the injection device (3) for the substance mixture (S) to be separated and at a distance therefrom there is provided a second separating path (4) for the further separation of the substance mixture (S) in an electric field applied along the second separating path (4). The second separating path (4) is inclined at an angle ($\alpha$) with respect to the first separating path (2). The region of intersection of the first (2) and second (4) separating paths forms a second injection device (5) for injecting the partially separated substance mixture (S) into a second carrier medium (E). The fluid substance mixture (S) is injected into the carrier medium (C) in the first injection device (3) and is then separated in the electric field that is applied along the first separating path (2). The partially separated substance mixture (S) is then injected into the second carrier medium (E) downstream of the first separating path (2) and further separated into its components in the electric field applied along the second separating path (4).

22 Claims, 2 Drawing Sheets

OTHER PUBLICATIONS

James W. Jorgenson et al "Automated Instrumentation for Comprehensive Two–Dimensional High–Performance Liquid Chromatography/Capillary Zone Electrophoresis" Analytical Chemistry, vol. 62, No. 10 (May 1990) 978–984.

James W. Jorgenson et al, "Two–Dimensional Protein Separation by Microcolumn Size–Exlusion Chromatography–Capillary Zone Electrophoresis" Journal of Chromatography (Feb. 1993) 213–220.

D. Kaniansky et al "Capillary Zone Electrophoresis of Complex Ionic Mixtures with On–Line Isotachophoretic Sample Pretreatment" Journal of Chromatography, 638 (May 1933) 137–146.

U. R. Tjaden et al, "Analyte Focusing in Capillary Electrophoresis Using On–Line Isotachophoresis" Journal of Chromatography, 591 (Feb. 1992) 341–349.

DEVICE AND A METHOD FOR THE ELECTROPHORETIC SEPARATION OF FLUID SUBSTANCE MIXTURES

The invention relates to a device and a method for the electrophoretic separation of fluid substance mixtures.

BACKGROUND

Electrophoretic separation methods are based on the different rates of migration of the individual components of a test sample in a carrier medium when an electric field is applied. A very widely used method is capillary electrophoresis in which a carrier medium and a sample to be tested are transported in a capillary system which comprises a capillary separating path between the ends of which the electric field is applied. The transport of the carrier medium in the capillary system and the injection of the sample to be tested into the carrier medium can be carried out with the aid of pumps and valves or using electric fields which are suitably applied in various portions of the capillary system. The individual components of the sample injected into the carrier medium migrate at different rates in the electric field of the separating path, with the result that the sample is separated. The individual components can be determined with the aid of a detector connected to the capillary separating path. For the simultaneous analysis of different samples there have also been proposed separating arrangements having several parallel capillaries (Anal. Chem. 1992, 64, 967–972).

In DNA sequencing, for example, gel-filled capillaries are used as the separating path. In that separating method the carrier medium, i.e. the gel, is not transported; instead only the sample injected into the gel migrates in the applied electric field. A typical separating performance (which is also referred to as the theoretical separating step number) of an electrophoretic separating system using such gel-filled capillaries is, for example, about 250 peaks in a period of 30 minutes.

U.S. Pat. No. 4,908,112 proposes the miniaturisation of branched capillary systems including the separating path. The capillary system is arranged on a semi-conductor chip. The transport of the carrier medium and the injection of the sample to be separated are effected with the aid of electric fields that can be switched between individual path portions of the capillary system. The dimensions of the channel system are very small but the field strengths that can be achieved are very high. Consequently only very small amounts of carrier medium and very small sample volumes are required. In addition, the separating method can be carried out very quickly at the high voltages applied, which are typically about 30 kV.

Another very widely used electrophoretic separating method is gel electrophoresis. That separating method, in which the separation of the sample into its constituents is effected not in solution but in a stationary carrier material, a gel, is also known as electropherography. In the electropherographic method the sample to be separated is applied as a strip preferably in the centre of a carrier material steeped in buffer (the pherogram) and an electrical voltage is applied to the ends of the carrier material. The sample is separated in accordance with the direction of migration and the rate of migration of the individual components. The differently charged components migrate to the respective oppositely charged poles, while the neutral components remain at the point of application. In a continuous separating method a buffer solution flows through a vertical plate of carrier material. The sample is added as near as possible to the upper end of the plate. The electrophoretic separation is brought about by an electric field applied perpendicularly to the flow of buffer.

Gel electrophoresis is an established separating method for charged biopolymers. Polyacrylamide gels (PAGE) are frequently used for the separation. The pore size of the polyacrylamide gels allows separation in accordance with the charge and the steric hindrance of the sample molecules in the gel. If sodium dodecyl sulfate (SDS) is added, good correlation is obtained between the migration distance of the separated sample molecules and the corresponding molar mass, which is, however, independent of the charge of the molecules. Isoelectric focussing (IEF or IF) as a preliminary stage before SDS-PAGE gel electrophoresis makes it possible also to separate many extremely complex substance mixtures.

A moderately well established further development of gel electrophoresis is so-called 2D gel electrophoresis in which a sample is separated in two dimensions (2D) in accordance with different criteria. Such a 2D gel electrophoresis separating arrangement is described, for example, in A. T. Andrews, "Electrophoresis, Theory, Techniques and Biochemical and Clinical Applications", Clarendon Press, Oxford 1986, pages 223–230. That two dimensional separating method is used especially as a combination of isoelectric focussing in the first dimension and gel electrophoresis, for example SDS-PAGE gel electrophoresis, in the second dimension. The resulting gel pattern provides in the first dimension information relating to the isoelectric point of the component in question and in the second dimension information relating to the molar mass of that component. A typical separating performance in 2D gel electrophoresis is a peak capacity of about 10 000 in a time period of more than 2 hours.

Although it is possible to obtain very high separating performances with 2D gel electrophoresis, a disadvantage of that method is that it is very slow. First of all the sample must be separated in the first dimension on a first gel. The first gel then has to be brought together with a second gel in which the separation in the second dimension is to take place, which is usually a laborious operation. The long analysis time results in the diffusion of the separated components in the free gel, which can lead to an undesirable broadening of the bands. The electrical voltage necessary for separation in the gel can be increased only to a limited extent and is typically about 2 kV. At higher voltages Joule effect heating occurs, which can result in the decomposition of the gel and the sample.

OBJECTS OF THE INVENTION

There is therefore no possibility of reducing the long analysis times required without at the same time losing resolution (separating performance). The very long analysis times are therefore a major obstacle to the use of 2D gel electrophoresis for the separation of highly complex substance mixtures.

In capillary electrophoresis the analysis time can be reduced significantly by increasing the voltage between the ends of the separating path. In the case of miniaturised capillary electrophoresis systems based on microchips, voltages of about 5 to 40 kV are typically used; this results in analysis times of less than one minute. However, only relatively simple substance mixtures can be separated using capillary electrophoresis. Coupling a large number of separating capillaries next to one another to achieve "two dimensionality" in order thus to be able also to separate highly complex substance mixtures would, however, require in the case of miniaturised systems connection pieces of sub-nanolitre volumes. Such connection pieces would, however, be very difficult and expensive to manufacture, if they could be manufactured at all. With very short capillary separating paths for very rapid separations, the disturbing effect of the dead spaces of the connection pieces is particularly high. Those dead spaces would therefore have to be kept vanishingly small, which appears to be impossible in practice. The construction of the separating path of a miniaturised capillary electrophoresis system as a flat bed, analogously to 2D gel electrophoresis, would promote the diffusion of the separated components and thus result in a marked impairment of the separating performance.

The problem underlying the invention is, therefore, to provide a device and a method for the electrophoretic separation of fluid substance mixtures, especially complex fluid substance mixtures, which have the same performance as 2D gel electrophoresis and which allow short separating and analysis times.

SUMMARY OF THE INVENTION

That problem and other problems are solved and the disadvantages of the devices and methods of the prior an are overcome by a device and by a method according to the latter part of patent claim 1 and of patent claim 19, respectively. Especially preferred embodiments and process variants of the invention are to be found in the respective dependent patent claims.

The invention provides especially a device for the electrophoretic separation of complex fluid substance mixtures which comprises a channel system for a carrier medium, an injection device for the injection into the carrier medium of a substance mixture to be separated, and a separating path for the separation of the substance mixture in an electric field applied along the separating path. Downstream of the injection device for the substance mixture to be separated and at a distance therefrom there is provided a second separating path for the further separation of the substance mixture in an electric field applied along the second separating path. The second separating path is inclined at an angle with respect to the first separating path. The region of intersection of the first and second separating paths forms a second injection device for injecting the partially separated substance mixture into a second carrier medium. The fluid substance mixture is injected into the carrier medium in the first injection device and is then separated in the electric field that is applied along the first separating path. The partially separated substance mixture is then injected into the second carrier medium downstream of the first separating path and is further separated into its components in the electric field applied along the second separating path.

The device according to the invention and the method according to the invention utilise the advantages of two-dimensional separation, as known from 2D gel electrophoresis, but do not have the disadvantage of the very long separating and analysis times. The advantages of very good separation also of highly complex substance mixtures is combined with the very short separating and analysis times made possible especially by miniaturised capillary electrophoresis systems. The invention provides a two-dimensional capillary electrophoresis system which does not require connection pieces of sub-nanolitre volumes. The method allows very rapid separations of a highly complex substance mixture which typically take less than one minute. The separating performances are significantly higher than in the case of conventional capillary electrophoresis. By virtue of the short analysis times, the invention can also be used for quasi-continuous analysis.

Preferably, the two injection devices for the injection of the substance mixture and the partially separated substance mixture have injection volumes that are defined by their geometry. In a preferred variant, the region of intersection of the first separating path with the second separating path is in the shape of a double-T piece, the crossbars of the T pieces each being formed by the second separating path. In this way the second separating path is of continuous construction, while the point at which the first separating path enters the second separating path and the point at which it branches Off from the second separating path for the removal of the mixture of the first carrier medium and the substance mixture to be separated are staggered with respect to one another along the length of the second separating path. For the purpose of injection into the second carrier medium the partially separated substance mixture is first transported at an angle to the transport direction in the first separating path. It is then diverted and transported, preferably in a direction parallel to the first separating path, to an outlet from the channel system. The first injection device is of entirely analogous construction. In that instance, the as yet unseparated substance mixture is first transported at an angle to the first separating path, then again diverted into the first transport direction and finally diverted again, at a branch downstream of the entry point into the fast separating path, and transported, preferably parallel to the original transport direction, to an outlet. In that way the injection is made block-fashion, the injected volume in each case being dependent upon the distance of the entry point from the associated exit point and upon the cross-section of the first and second separating paths.

In a preferred variant, the fast and second injection devices have the shape of a double-T piece, the crossbars of the T pieces each being formed by the first or the second separating paths or the rectilinear extensions thereof.

In an especially preferred variant of the invention there are provided downstream of the first injection device further separating paths for the further separation of the substance mixture in an electric field applied along the respective separating path. Those separating paths likewise extend at an angle to the fast separating path and approximately parallel to one another. The regions of intersection of the further separating paths with the first separating path each form further injection devices at which the partially separated substance mixture is injected into a second carrier medium transported through the further separating paths. The construction of the injection devices in this case preferably corresponds to that already described above. This especially preferred variant enables the device to be used for a particularly wide variety of applications. In particular, it is possible for various components of the substance mixture that has been partially separated in the first separating path to be injected into the further separating paths that intersect one after another downstream and extend parallel to one another, and for those components there to be subjected to further separation in accordance with particular criteria. For example, different field strength distributions can apply in the individual further separating paths, a circumstance which can have a decisive effect on the further separation of the substance mixture.

Preferably, the ends of the further separating paths terminate in a common reservoir and a common collecting vessel for the second carrier medium. The reservoir and the collecting vessel are preferably of larger cross-section than are the capillary-form separating paths in order to provide an adequate supply of carrier medium for the separating paths and to prevent backing up, respectively. The cross-section of the supply and removal capillaries is preferably selected to be from about 2 to about 10 000 times greater than the cross-section of the separating paths. As a result, troublefree operation is ensured even with relatively viscous carrier media.

There is scope for employing the separating device according to the invention in an especially interesting way if means are provided that allow a pH gradient to be established in the second carrier medium in the reservoir and in the collecting vessel. For that purpose, for example, ampholytes are used as the second carrier medium. Electrodes allow an electric field to be generated in the ampholyte in the reservoir and in the collecting vessel. The acidic and basic groups of the molecules of the ampholyte align themselves accordingly in the electric field, migrate and in that way generate a temporary or stable pH gradient in the ampholyte. In the device so modified, the carrier medium flowing through each further separating path has a different pH value. In that way the partially separated substance mixture injected can be further separated under different marginal conditions in each separating path.

In order to ensure that the separation of the substance mixture in the first and in the further separating paths takes place in accordance with different criteria, the first carrier medium in the first separating path is selected to be different from that in the further separating paths. The carrier media selected are preferably electrolyte solutions or gels. For example, isoelectric focussing of the substance mixture can take place in the first separating path (first dimension), with the actual separation into the individual components then taking place in the further separating paths (second dimension).

The separated components of the substance mixture are preferably either detected optically two-dimensionally in two spatial coordinates at a certain time point with the aid of a camera or are detected using a linear-scanning optical detector by means of the detection of the spatial and time coordinates. Both detection methods are readily integrable and are compatible with digital evaluating devices.

In an especially preferred variant the separating device according to the invention is miniaturised. The channel system, the injection devices, the separating paths and the supply and removal capillaries are made in a plate of glass, polymer film or a semiconductive material, preferably monocrystalline silicon, which can, if desired, be covered with a lid, preferably of glass. In the lid and/or in the plate there are provided separate inflow and outflow openings for the first and second carrier media and for the substance mixture to be separated. The separating paths are preferably in the form of grooves the depth of which is from approximately 0.1 µm to approximately 1000 µm and the width of which is from approximately 1 µm to approximately 500 µm. The narrower the channel, the deeper it is and vice versa. The miniaturised separating device so constructed can be mass-produced using the customary micromechanical manufacturing methods or using manufacturing methods known from the semiconductor industry and is therefore relatively inexpensive to produce. In addition, it is possible for various electronic elements, for example electrodes for transporting the carrier medium by means of electric fields etc., to be integrated on the "analysis chip".

In a variant of the device, the carrier media used are preferably aqueous electrolytes. These have the advantage that they can be transported through the channel system and the separating paths with the aid of electric fields. The electric fields required for that purpose can be generated and controlled, for example, by means of electrodes integrated on the miniaturised analysis chip. Where the channels and separating paths are of suitably small cross-section they may also be open on one or two sides. In that case the carrier medium and the samples remain in the channels and the separating paths as a result of the prevailing capillary forces.

It is also possible to use gels as carrier media. These are preferably stationary, that is to say that in this case the carrier medium is not transported through the channel system and the separating paths but instead only the sample migrates in the gel. In that case the channel system and the separating paths can be open on one, two or even three sides. The entire channel system and the separating paths can be made in the gel or gels, for example, by photolithography or by printing or embossing techniques. The gel itself forms the channel system and the separating paths, and in the case of the variant that is open on three sides it is only the non-conductive carrier material for the gel that additionally defines the channels. The samples in that case migrate in the gel channels without further lateral guidance.

The angle at which the second separating path(s) is(are) inclined with respect to the first separating path is about 30°–150°, preferably about 90°. This allows a relatively great degree of flexibility in the shaping and arrangement of the channels and separating paths, and the two-dimensionality of the separating process is retained.

The device is preferably also equipped with at least one detector for the substance mixture that has been separated into its components. This may be, for example, an optical detector or a detector functioning on an electrochemical basis. In that way the device can be tailored to very specific analyses; according to the nature of the detector it is possible, for example, to detect very specific components. Because the design concept allows the device to be miniaturised, there is scope for a wide variety of uses, for example, in technological, scientific and also medical fields.

BRIEF DESCRIPTION OF THE DRAWINGS

The device according to the invention with all its essential parts is described in greater detail below by way of example with reference to variants shown in diagrammatic form. The principles of the method according to the invention will also be explained with reference to the drawings.

DETAILED DESCRIPTION OF PREFERRED EMBODIMENTS

Figure 1:
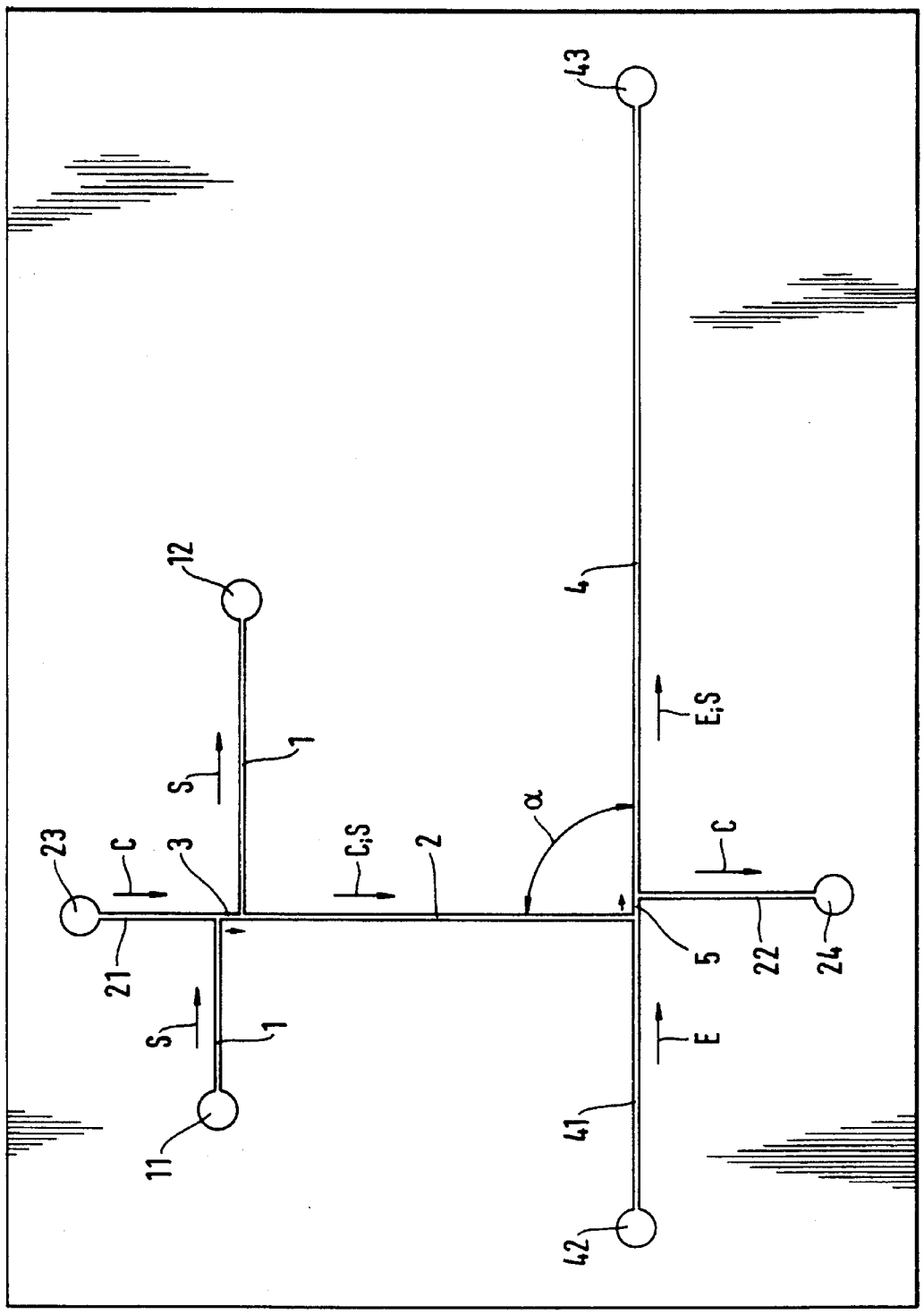
FIG. 1 is a first embodiment of the separating device.

The embodiment shown in FIG. 1 illustrates the basic principle underlying the device according to the invention for the electrophoretic separation of fluid substance mixtures, especially highly complex fluid substance mixtures. The device comprises a capillary system for the transport of a carrier medium C and of a substance mixture S to be separated, an injection device 3 for the injection of the substance mixture S to be separated into the carrier medium C, and a preferably capillary-form separating path 2 which forms part of the capillary system. During its transport through the separating path 2 the substance mixture is separated in an electric field applied along the separating path. For reasons of clarity the electrodes used to generate the electric field along the separating path 2 are not shown the diagram, the carrier medium C and the substance mixture S and the directions of flow thereof are indicated by arrows appropriately labelled S and C. The ends of the capillary portions 21 and 22 terminate in inlets and outlets 23 and 24, respectively, by means of which the fluid, preferably liquid, carrier medium C can be introduced into the capillary system and also removed again. In corresponding manner the ends of the capillary portion 1 terminate in an inlet 11 and an outlet 12 for the substance mixture S to be separated.

The region of intersection between the capillary portions 1 by means of which the substance mixture S is transported and the capillary portion 21,2,22 in which the carrier medium C is transported, forms the injection device 3 for injecting the substance mixture S into the flow of carrier medium C. The region of intersection can be in the form of a simple, rectilinear intersection, but it is preferably constructed in such a manner that the injection device 3 for the injection of the substance mixture S to be separated into the carrier medium C has a geometrically defined injection volume. For that purpose the region of intersection is in the form of a double-T piece, the crossbars of the T pieces each being formed by the first separating path 2 or the rectilinear extension thereof 21. The injection volume is in that way fixed by the distance between the point of entry of the channel portion 1 into the separating path 2 and its outlet opening, which is arranged for example downstream, and by the cross-section of the separating path 2.

According to the invention, downstream of and at a distance from the injection device 3 there is arranged a second, preferably capillary-form, separating path 4 which is inclined at an angle α with respect to the first separating path and which in this embodiment extends preferably approximately perpendicularly with respect to the first separating path 2. The second separating path 4 extends in preferably rectilinear extension into a capillary piece 41. The second separating path 4 and the capillary piece 41 likewise form part of the capillary system of the device. The ends of the capillary piece 41 and of the second separating path 4 terminate in inlet and outlet openings 42 and 43, respectively, by means of which a second fluid, preferably liquid, carrier medium E can be introduced into the capillary system and removed again therefrom.

The region of intersection of the first and second separating paths 2, 4 is constructed in such a manner that it forms a second injection device 5 for injecting the partially separated substance mixture S into the second carrier medium E transported along the second separating path 4. The region of intersection can be in the form of a simple rectilinear intersection, but it is preferably constructed in such a manner that the injection device 5 for the injection of the partially separated substance mixture S into the second carrier medium E has a geometrically defined injection volume. For that purpose the region of intersection is in the form of a double-T piece, the crossbars of the T pieces each being formed by the second separating path 4 or the rectilinear extension thereof, the capillary piece 41. The injection volume is in that way fixed by the distance between the point of entry of the first separating path 2 into the second separating path 4 and the opening, which is arranged for example downstream, of the capillary portion 22 which leads into the outflow 24 for the first carrier medium C, and by the cross-section of the second separating path 4.

The substance mixture S that has been partially separated in the first separating path 2 is injected at the second injection device 5 into the flow of second carrier medium E and further separated into its components in an electric field applied along the second separating path 4. For reasons of clarity the electrodes used to generate the electric field along the separating path 4 are not shown. The first carrier medium C is preferably different from the second E. In that way the first and the second separations can be effected in accordance with different criteria. For example, first of all isoelectric focussing of the substance mixture can be effected in the first separating path 2, with the actual separation into the individual components taking place in the subsequent, second separating path 4.

Figure 2:
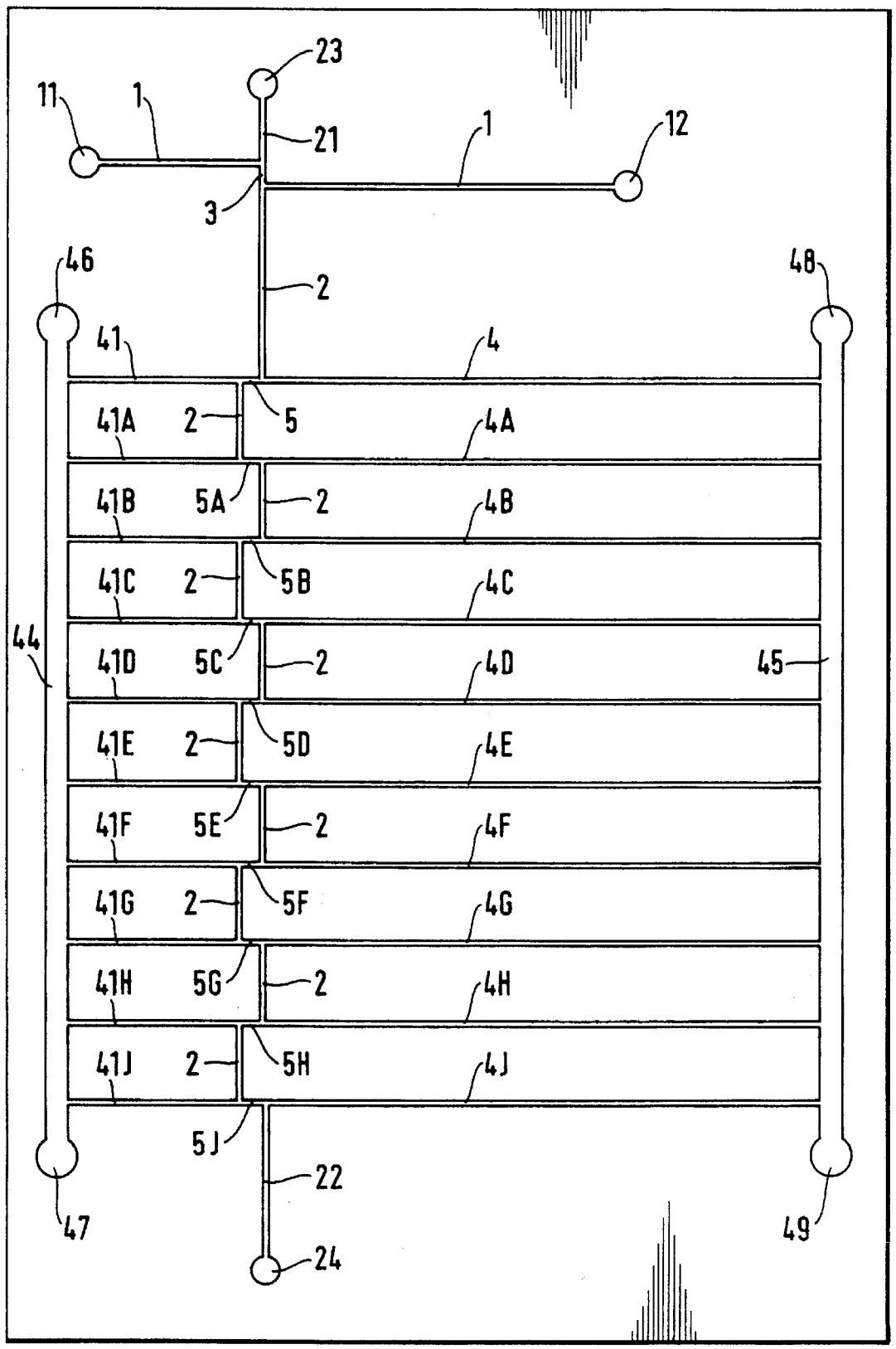
FIG. 2 is a second embodiment of the device according to the invention.

The embodiment of the device according to the invention shown in FIG. 2 is a futher development of the example from FIG. 1 illustrating the principle. Following the first separating path 2 there is arranged downstream a series of futher separating paths 4, 4A–4J. The additional separating paths 4, 4A–4J all extend approximately perpendicularly with respect to the first separating path 2 and approximately parallel to one another. The regions of intersection of the additional separating paths 4, 4A–4J with the first separating path 2 form injection devices 5, 5A–5J for the partially separated substance mixture S. As explained in connection with the embodiment of the principle, the injection volume of the injection devices 5, 5A–5J is preferably geometrically defined. All regions of intersection are therefore preferably in the form of double-T pieces, the crossbars of the Ts each being formed by the respective additional separating paths 4, 4A–4J or the rectilinear extensions thereof, the capillary pieces 41, 41A–41J.

The ends of the additional separating paths 4, 4A–4J and the ends of the capillary pieces 41, 41A–41J terminate in a common reservoir 44 for the second carrier medium E and in a common collecting vessel 45. In a special case the common reservoir 44 is in the form of a supply capillary and the common collecting vessel 45 in the form of a removal capillary. The capillaries 44, 45 are of larger cross-section than are the separating paths 2 and 4, 4A–4J. The two ends of the supply capillary 44 are connected with openings 46 and 47 by means of which the second carrier medium is fed into the supply capillary 44. The two ends of the removal capillary 45 terminate in outlet openings 48 and 49 by means of which the carrier medium/substance mixture E+S is transported out of the removal capillary 45 again. The pre-separated substance mixture S is injected into a plurality of further separating paths 4, 4A–4J which extend parallel to one another, where it is subjected to further separation in parallel. By a suitable choice of the injection time point it is possible to inject quite specific "pre-components" of the substance mixture from the first separating path 2 into the further separating paths 4, 4A–4J where they are further separated. It is also possible to carry out the further separation in the individual further separating paths 4, 4A–4J in electric fields of different strengths.

The embodiment of the invention according to FIG. 2 can also be modified to the effect that the second carrier medium E in the supply and in the removal capillary 44, 45 has a pH gradient. Care should be taken that the pH value of the second carrier medium in the supply capillary and of that in the removal capillary has the same gradient curve. In this way each of the additional separating paths 4, 4A–4J can be supplied with carrier medium of a different pH value. The separation of the pre-separated substance mixture is then effected in each of the additional separating paths 4, 4A–4J in a carrier medium of a different pH value, that is to say under controllably different conditions.

In a simplified variant of the second embodiment the substance mixture S is not subjected to pre-separation but is fed into the capillary system directly via the inflow 23, instead of via a first carrier medium C, and injected into the further separating paths 4, 4A–4J at the injection devices 5, 5A–5J. In this simplified embodiment having no pre-separation it is also possible to dispense with the capillary portion 1 by means of which the substance mixture S is normally introduced into the first separating path 2. The design concept of the device according to the invention also enables the capillary system, the injection devices 3, 5, 5A–5J, the separating paths 2, 4, 4A–4J and the supply and removal capillaries 44, 45 to be made in a plate of glass or a semi-conductive material, preferably monocrystalline silicon. The separating paths are in the form of grooves the width of which is from approximately 1 µm to approximately 500 µm, and the depth of which is from approximately 0.1 µm to approximately 1000 µm. The plate can be covered on the side having the grooves with a lid, preferably of glass. In the lid and/or in the plate there are provided the inflow and outflow openings 23, 24; 42, 43; 46–48; 11, 12 for the first and second carrier media C, E and for the substance mixture S to be separated. They are preferably in the form of openings for inserting connection capillaries.

In order to detect the individual components of the separated substance mixture there is provided a detector (not shown in the Figures) for the substance mixture that has been separated into its components. The detector is, for example, an optical camera by means of which the separated components are detected two-dimensionally in two spatial coordinates at a certain time point. Alternatively, the separated components of the substance mixture S can be detected using a linear-scanning optical detector by means of the detection of the spatial and time coordinates.

The device according to the invention and the method according to the invention allow two-dimensional electrophoresis of highly complex substance mixes in a capillary electrophoresis system. High separating performances are obtained without the need to accept the long separating and analysis times known from 2D gel electrophoresis. The device and the method have a wide variety of applications. The choice of carrier media depends upon the substance mixture to be separated. It is possible to use suitable electrolyte solutions or gels with or without pH gradients. The "Journal of Chromatography Library"—Vol. 52, Capillary Electrophoresis, 1992 Elsevier Science Publishers B. V., pages 173–183 gives examples of gels that can also be used with the device according to the invention. The miniaturised variant allows the use of micromechanical mass production techniques and mass production techniques known from semi-conductor manufacture. As a result, the device according to the invention can be produced in large numbers at relatively low cost. The miniaturised variant in the form of an "analysis chip" additionally allows the on-chip integration of electric components, for example the electrodes for generating the field in the separating paths.

What is claimed is:

1. A device for the electrophoretic separation of complex fluid substance mixtures, comprising a channel system for carrier media, an injection device for the injection into a first carrier medium of a substance mixture to be separated, and a first separating path for the separation of the substance mixture in an electric field that is applied in the first carrier medium along the first separating path, wherein for the further separation of the substance mixture there is provided at least one second separating path having a second carrier medium, which second carrier medium is different from the first carrier medium, in which a further electric field is applied along the second separating path, which second separating path is inclined at an angle with respect to the first separating path and, downstream of and at a distance from the injection device for the substance mixture to be separated, extends in such a manner that the region of intersection of the first separating path with the second separating path forms a second injection device for injecting the partially separated substance mixture into the second carrier medium wherein the injection volume of the second injection device is the volume of the second separating path between a point of entry of the first separating path into the second separating path and an opening in the second separating path which leads to an outflow for the first carrier medium.

2. A device according to claim 1, wherein the region of intersection of the first separating path with the second separating path is in the shape of a double-T piece, the crossbars of the T pieces each being formed by the second separating path or the rectilinear extension thereof.

3. A device according to claim 2, wherein the first injection device has the shape of a double-T piece, the crossbars of the T pieces each being formed by the first separating path or the rectilinear extension thereof.

4. A device according to claim 1, wherein downstream of the first injection device there is provided a number of further separating paths for the further separation of the substance mixture in an electric field applied along the respective separating path, which further separating paths are inclined at an angle with respect to the first separating path and are arranged approximately parallel to one another, their regions of intersection with the first separating path each forming further injection devices for injecting the partially separated substance mixture into a second carrier medium.

5. A device according to claim 4, wherein the ends of the further separating paths terminate in a common reservoir and a common collecting vessel for the second carrier medium which are preferably of larger cross-section than are the separating paths.

6. A device according to claim 5, wherein the cross-section of the reservoir and of the collecting vessel is approximately from 2 to 10 000 times greater than the cross-section of the separating paths.

7. A device according to claim 5, wherein the resevoir and the collecting vessel are equipped with means that allow a pH gradient to be established in the second carrier medium.

8. A device according to claim 5, wherein the channel system the injection devices the separating paths and where appropriate the reservoir and the collecting vessel and any other extension channels are made in a plate of glass, a polymer film or a semi-conductive material, preferably monocrystalline silicon, which can preferably be covered with a lid, for example of glass, and wherein separate inflow and outflow openings are provided for the first and second carrier media and for the substance mixture to be separated, which inflow and outflow openings are arranged in the lid and/or in the plate.

9. A device according to claim 8, wherein the separating paths are in the form of grooves the depth of which is from approximately 0.1 µm to approximately 1000 µm and the width of which is from approximately 1 µm to approximately 500 µm.

10. A device according to claim 1, wherein the carrier media arepreferably aqueous electrolytes which are transported through the channel system and the separating paths with the aid of electric fields.

11. A device according to claims 1, wherein the carrier media are stationary gels.

12. A device according to claim 1, wherein the angle at which the second separating path or the further separating paths is(are) inclined with respect to the first separating path is about 30° to 150°.

13. A device according to claim 12, wherein the angle is about 90°.

14. A device according to claim 1, wherein a detector is provided for the substance mixture that has been separated into its components.

15. A method for the electrophoretic separation of complex fluid substance mixtures along separating paths, in which a complex substance mixture is injected into a first carrier medium upstream of a first separating path and is then separated in an electric field that is applied along the first separating path, wherein the partially separated substance mixture is injected into a second separating path having a second carrier medium, which second carrier medium is different from the first carrier medium, and which second separating path intersects with the first separating path and inclines at an angle with respect to the first separating path such that the region of intersection of the first separating path with the second separating path forms an injection device having an injection volume which is the volume of the second separating path between a point of entry of the first separating path into the second separating path and an opening in the second separating path which leads to an outflow for the first carrier medium, and wherein the substance mixture is further separated in an electric field applied in the second carrier medium along the second separating path.

16. A method according to claim 15, wherein the partially separated substance mixture is injected into a number of further separating paths arranged one after the other downstream of the first separating path and extending approximately parallel to one another and at an angle with respect to the first separating path, where it is subjected to further separation in parallel in the respective electric fields applied.

17. A method according to claims 16, wherein the pH value of the second carrier medium is influenced in such a manner that the second carrier medium in each of the individual separating paths has a different pH value, and wherein a pH gradient is established between the carrier media present in adjacent separating channels.

18. A method according to claim 15, wherein the partially separated substance mixture in the second separating path(s) is moved in a direction that forms an angle of about 30° to 150°, with its direction of movement in the first separating path.

19. A device according to claim 18, wherein the angle is about 90°.

20. A method according to claim 15, wherein the carrier media selected are mobile electrolyte solutions or preferably stationary gels.

21. A method according to claim 19, wherein the injection device for the injection of the partially separated substance mixture into the second separating path is in the shape of a double-T piece, the crossbars of the T pieces each being formed by the second separating path or the rectilinear extension thereof.

22. A method for the electrophoretic separation of complex fluid substance mixtures along separating paths, in which a complex substance mixture is injected into a first carrier medium upstream of a first separating path and is then isoelectrically focused in an electric field that is applied along the first separating path, wherein the isoelectrically focused substance mixture is injected into a second separating path having a second carrier medium, which second carrier medium is different from the first carrier medium, and which second separating path intersects with the first separating path and inclines at an angle with respect to the first separating path such that the region of intersection of the first separating oath with the second separating path forms an injection device having an injection volume which is the volume of the second separating path between a point of entry of the first separating path into the second separating path and an opening in the second separating path which leads to an outflow for the first carrier medium, and wherein the substance mixture is separated in an electric field applied in the second carrier medium along the second separating path.

* * * * *